United States Patent
Barnes et al.

(10) Patent No.: US 6,893,260 B2
(45) Date of Patent: May 17, 2005

(54) DENTAL INSTRUMENT

(75) Inventors: Virginia Monsul Barnes, Annandale, NJ (US); Tao Xu, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/630,157

(22) Filed: Jul. 30, 2003

(65) Prior Publication Data

US 2005/0026105 A1 Feb. 3, 2005

(51) Int. Cl.$^7$ ............................................... A61C 19/04
(52) U.S. Cl. ...................................................... 433/72
(58) Field of Search ......................... 433/72, 141, 143; 33/513, 514

(56) References Cited

U.S. PATENT DOCUMENTS

| | | | | |
|---|---|---|---|---|
| 1,003,213 A | * | 9/1911 | Skinner | 433/143 |
| 1,743,154 A | * | 1/1930 | Meyer | 433/141 |
| 3,935,640 A | | 2/1976 | Cohan | 32/40 |
| 4,552,531 A | | 11/1985 | Martin | 433/147 |
| 5,004,419 A | * | 4/1991 | Kline | 433/143 |
| 5,096,420 A | | 3/1992 | Loewenthal | 433/72 |
| 5,178,537 A | | 1/1993 | Currie | 433/72 |
| 5,193,999 A | | 3/1993 | Staubli | 433/72 |
| 5,244,386 A | | 9/1993 | Angelo | 433/72 |
| 5,271,734 A | | 12/1993 | Takeuchi | 433/72 |
| 5,587,284 A | | 12/1996 | Brattesani | 433/72 |
| 5,676,544 A | | 10/1997 | Urban | 433/147 |
| 5,725,373 A | | 3/1998 | Yeh | 433/72 |
| 6,024,564 A | | 2/2000 | Kesling | 433/72 |
| 6,116,899 A | | 9/2000 | Takeuchi | 433/72 |
| 6,123,546 A | | 9/2000 | Bergstrom | 433/72 |
| 6,241,519 B1 | | 6/2001 | Sedelmayer | 433/72 |
| 6,409,505 B1 | | 6/2002 | Kesling | 433/72 |

OTHER PUBLICATIONS

ISBN 0-8016-0980-1—Loretta Carter and Peter Yaman, Dental Instruments, pp. 120,121.

* cited by examiner

Primary Examiner—Cary E. O'Connor
(74) Attorney, Agent, or Firm—Harris A. Wolin; Clifford E. Wilkins

(57) ABSTRACT

This invention is directed to a dental instrument and the use of this dental instrument to measure deposits and other imperfections on a tooth surface. The dental instrument has an elongated portion and on at least one end a general curvature portion. The general curvature portion will have the general curvature of a posterior tooth or an anterior tooth. Preferably it also will be marked with measured segments. By placing the general curvature portion against a tooth a deposit or imperfection on a tooth can be measured. In a preferred embodiment the dental instrument will have a general curvature portion in each end; the general curvature on one end being for posterior teeth and the general curvature on the other end being for anterior teeth. When measuring plaque and related deposits a dye solution can be used to make the deposit more visible.

18 Claims, 3 Drawing Sheets

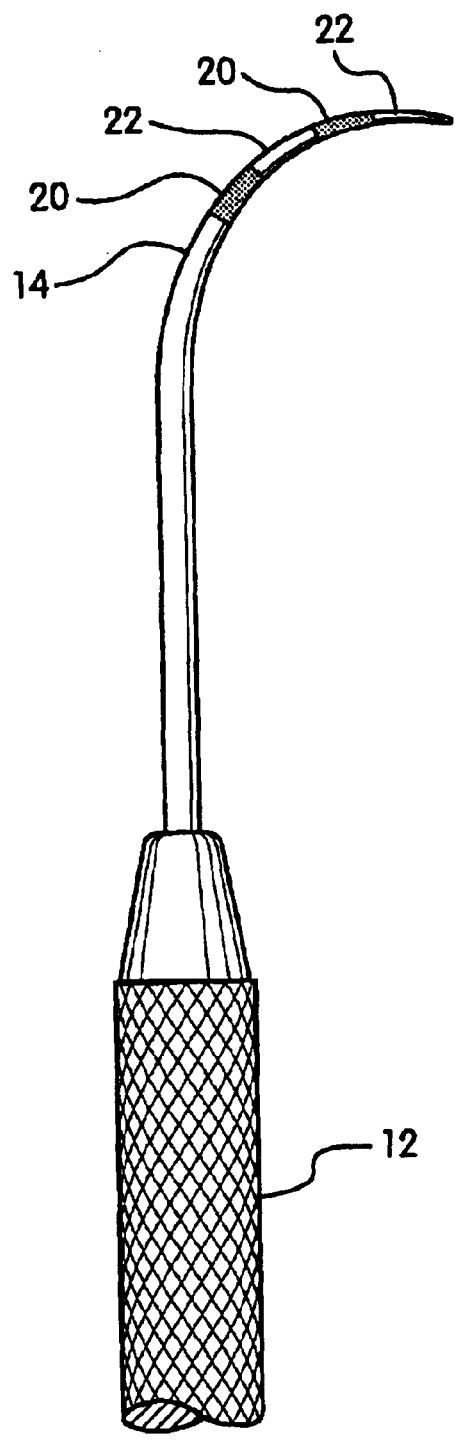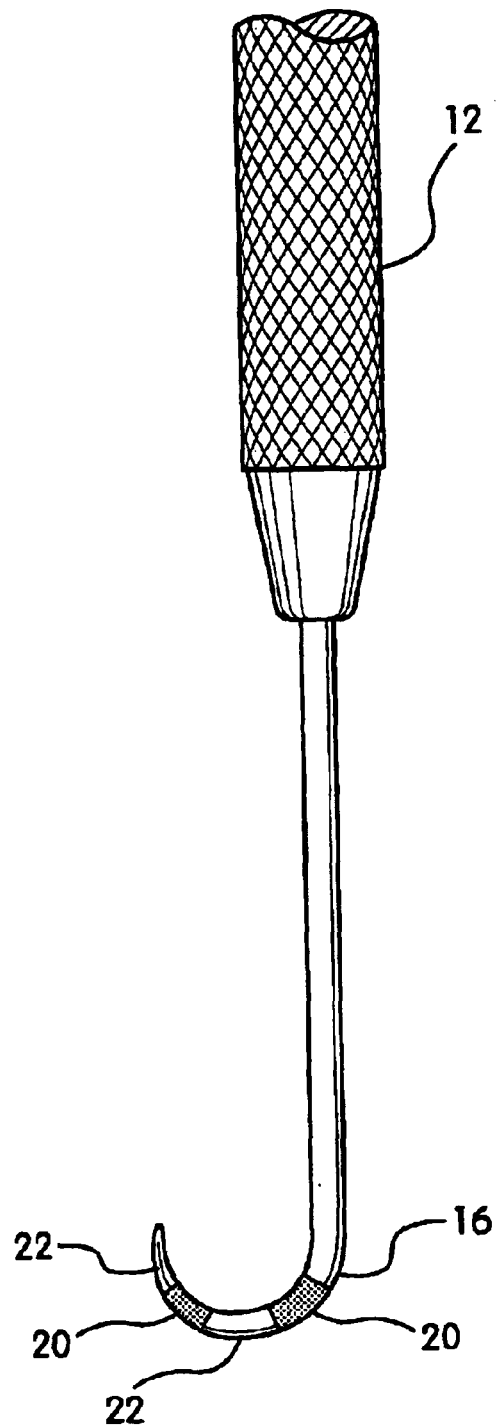
Fig. 2
Fig. 3

DENTAL INSTRUMENT

This invention relates to a dental instrument for the measurement of deposits or imperfections on a tooth, and the method for making such measurements. More particularly it relates to a dental instrument having generally curved portions on one or both ends, the curved portions being of a curvature similar to that of posterior or anterior teeth and its use for making measurements.

BACKGROUND OF THE INVENTION

These are a variety of dental probes and picks that are used by dentists in the treatment of teeth and gums. These probes are used to measure gum recession, bone loss or comprise a root canal condenser. The probes have ends with a narrow cross-section to be inserted into the gingival pocket to measure the depth of this pocket. The measuring is by visually seeing measured segments on the probe. These probes have an end that is at a right or oblique angle and is substantially straight. It will have measured segments so that the depth of the gingival recession can be measured. Exemplary of these probes are those of U.S. Pat. No. 4,552,531, U.S. Pat. No. 5,096,420 and U.S. Pat. No. 5,178,537. A related dental instrument is serpentine in shape and is for periodontal cleaning and measurement and is shown in U.S. Pat. No. 5,676,544. This probe extends below the gum line to the root area of the tooth to measure the extent the gum has receded and the amount of bone loss. None of these instruments or probes can be easily used to provide accurate information on deposits or imperfections on teeth above the gum line. This particularly is the case for the measurement of plaque and tartar on tooth surfaces. The dental instrument of this invention solves the problem.

BRIEF SUMMARY OF THE INVENTION

The present dental instrument is very effective in measuring deposits and imperfections on teeth. The deposits can be plaque and tartar. The imperfections can be stains or tooth repair fillings. This dental instrument simplifies the measurements of these deposits and imperfections.

The dental instrument has an elongated portion and at least one curved portion on an end. The curved portion has the general curvature of a posterior tooth or an anterior tooth. Preferably there is a curved portion in each end of the elongated portion, one to measure posterior teeth and one to measure anterior teeth.

The curved portions in a preferred embodiment will have measured segments to aid in the measurement of the deposits or imperfections. The measured segments will be in lengths of from about 1 mm to about 10 mm, and preferably about 2 mm to 6 mm.

In use to measure plaque or tartar the curved portion will be placed along the surface of the tooth, usually about parallel to the gum line, and a measurement taken using the measured segments as a guide. An end with the larger radius will be used for posterior teeth and an end with the smaller radius for anterior teeth. This procedure can be used for measuring deposits with or without the use of a dye containing disclosing solution. In the use of a disclosing solution the deposit will take up the dye and be more visible and facilitate measurement.

Although directed primarily to the measurement of tooth deposits and imperfections it also can be used in various periodontal procedures.

BRIEF DESCRIPTION OF THE INVENTION

FIG. 2 is a view of the end of the dental instrument end for measuring posterior teeth in an enlarged view.

FIG. 3 is a view of the end of the dental instrument end for measuring anterior teeth in an enlarged view.

DETAILED DESCRIPTION OF THE INVENTION

Figure 1:
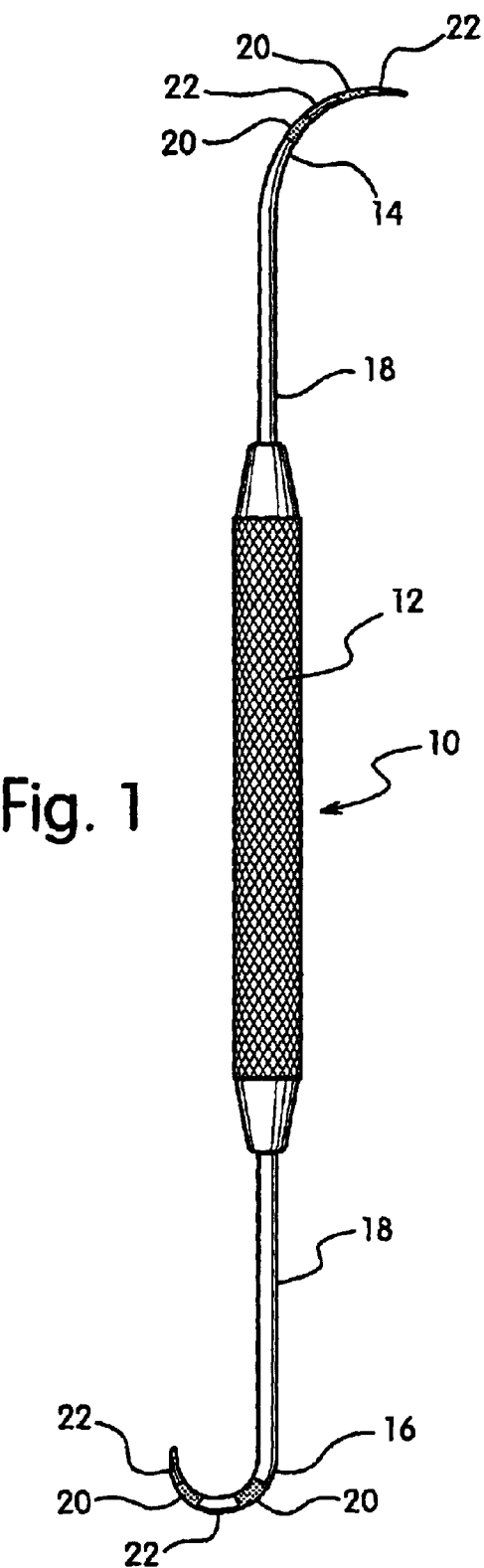
FIG. 1 is plan view of the dental instrument of this invention.

The invention now will be described in more detail in its preferred embodiments with reference to the Figures in the drawings.

FIG. 1 shows the dental instrument 10 which is comprised of an elongated grip portion 12 and curved portion 14 on one end and curved portion 16 in the other end. Sections 18 connect the curved portions 14 and 16 to the grip portion 12. Curved portion 14 is the general curvature of posterior teeth and curved portion 16 is the general curvature of anterior teeth. Each of these curved portions has measured segments 20 and 22. These segments are in gradations of about 0.5 mm to about 10 mm, and preferably about 1 mm to about 6 mm. FIGS. 2 and 3 show each of these curved portions 14 and 16 in an enlarged view. The measured segments also are shown in more detail in these views.

Figure 4:
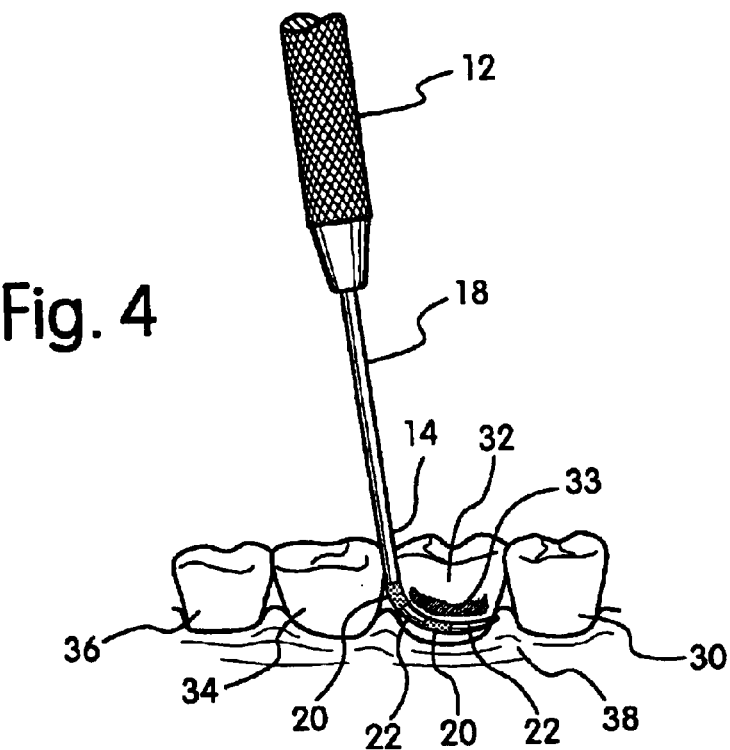
FIG. 4 is a view of the dental instrument against a posterior tooth to measure a plaque deposit.

FIG. 4 illustrates the curvature portion 14 against a posterior tooth 32 to measure the plaque deposit 33 on the tooth. Also shown are adjacent teeth 30, 34 and 36 and gum area 38. By counting the gradations 20, 22 adjacent the plaque deposits an accurate reading of the amount of plaque on the tooth can be obtained.

Figure 5:
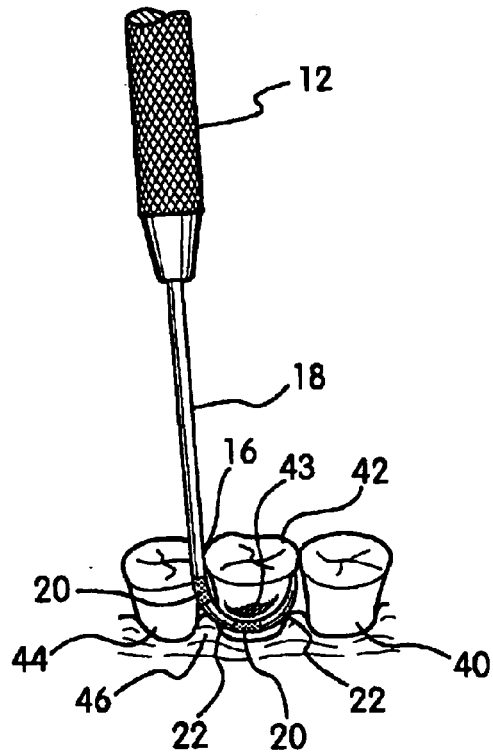
FIG. 5 is a view of the dental instrument against an anterior tooth to measure a plaque deposit.

FIG. 5 illustrates the curvature portion 16 against an anterior tooth to measure the plaque deposit 43 on tooth 42. Also shown in this view are adjacent teeth 40 and 44 and gum area 46. By counting the gradations 20, 22 adjacent the plaque deposit an accurate reading of the amount of plaque on the tooth can be calculated.

The probe can be made out of any of the common materials used to make probes. These usually will be metal with stainless steel being preferred. The use of stainless steel results in a stronger and longer lasting probe.

The use of this new probe results in less time to conduct clinical studies, patient diagnosis and provides more accurate results for such studies and diagnosis.

A study was conducted of the use of a fluoride containing dentifrice against the Colgate Total dentifrice. Fifteen panelists were in the study. The panelists refrained from any oral cleaning for 24 hours. Each then gargled with a red dye disclosing solution. It was found that the decrease in plaque with the Colgate Total dentifrice was 35.67% for the fluoride dentifrice Colgate Total 15.57% . The P value of the data was <0.01%.

What is claimed is:

1. A dental instrument for measuring deposits along the gingival surface of a tooth comprising:

an elongated portion defined along a longitudinal axis of the instrument;

a first curved portion on one end of said elongated portion and having a first radii of curvature; and a second curved portion on the opposite end of said elongated portion and having a second radii of curvature that differs from said first radii of curvature;

wherein at least one of said first and second curved portions is marked with measured segments that follow the radii of curvature of the curved portions so that the deposit measured along the gingival surface of the tooth is determined by counting the measured segments.

2. A dental instrument as in claim 1 wherein said first radii of curvature is that of posterior teeth.

3. A dental instrument as in claim 1 wherein said second radii of curvature is that of anterior teeth.

4. A dental instrument as in claim 1 wherein at least one curved portion extends tangentially from the elongated portion such that each curved portion does not intersect said longitudinal axis.

5. A dental instrument as in claim 4 wherein each curved portion extends tangentially from the elongated portion such that each curved portion does not intersect said longitudinal axis.

6. A dental instrument as in claim 1 wherein each of the curved portions is marked with measured segments.

7. A dental instrument as in claim 1 wherein said first curved portion is marked with measured segments.

8. A dental instrument as in claim 1 wherein said second curved portion is marked with measured segments.

9. A method of measuring a deposit on a tooth comprising:
   (a) treating the tooth so that the deposit can be visualized;
   (b) contacting the tooth with a curvature portion of a dental instrument having an elongated portion and a curvature portion, the curvature portion having the general curvature of the tooth undergoing measurement and being marked with measured segments; and
   (c) reading the number of measured segments that coincide with the deposit.

10. A method as in claim 9 wherein said tooth is treated with a solution and absorbs a dye from said solution.

11. A method as in claim 9 wherein said dental instrument has an elongated portion with a general curvature portion on at least one end.

12. A method as in claim 11 wherein said dental instrument has a general curvature portion at one end and another end.

13. A method as in claim 12 wherein each general curvature portion has marked segments.

14. A method as in claim 9 wherein said general curvature portion has measured segments.

15. A dental instrument for measuring deposits along the gingival surface of a tooth comprising:
   an elongated portion defined along a longitudinal axis of the instrument;
   a first curved portion on one end of said elongated portion and a second curved portion on the opposite end of said elongated portion;
   at least one of said first and second curved portions is marked with measured segments so that the deposit measured along the gingival surface of the tooth is determined by counting the measured segments; and
   wherein each curved portion extends from the elongated portion and does not intersect said longitudinal axis or point in a direction that intersects said longitudinal axis.

16. A dental instrument in accordance with claim 15, further comprising measured segments on the first and second curved portions.

17. A dental instrument in accordance with claim 16, wherein the first and second curved portions have different radii of curvature.

18. A dental instrument in accordance with claim 17, wherein the measured segments are curved and follow the radii of curvature of each of the curved portions.

* * * * *